(12) United States Patent
Pavlakovic (10) Patent No.: US 9,065,038 B2
(45) Date of Patent: Jun. 23, 2015

(54) TRANSDUCER ASSEMBLY

(75) Inventor: Brian Nicholas Pavlakovic, London (GB)

(73) Assignee: GUIDED ULTRASONICS LTD., Nottingham (GB)

( * ) Notice: Subject to any disclaimer, the term of this patent is extended or adjusted under 35 U.S.C. 154(b) by 431 days.

(21) Appl. No.: 13/640,946

(22) PCT Filed: Feb. 28, 2011

(86) PCT No.: PCT/GB2011/050395
§ 371 (c)(1),
(2), (4) Date: Feb. 5, 2013

(87) PCT Pub. No.: WO2011/131954
PCT Pub. Date: Oct. 27, 2011

(65) Prior Publication Data
US 2013/0127296 A1    May 23, 2013

(30) Foreign Application Priority Data

Apr. 20, 2010    (GB) .................................. 1006571.2
Sep. 17, 2010    (GB) .................................. 1015609.9

(51) Int. Cl.
*H01L 41/08* (2006.01)
*H04R 17/00* (2006.01)
*G01N 29/265* (2006.01)
*H01L 41/053* (2006.01)
*G01N 29/07* (2006.01)
*G01N 29/24* (2006.01)

(52) U.S. Cl.
CPC ............ *H01L 41/0533* (2013.01); *G01N 29/07* (2013.01); *G01N 29/2437* (2013.01); *G01N 29/265* (2013.01); *G01N 2291/0289* (2013.01); *G01N 2291/2634* (2013.01)

(58) Field of Classification Search
USPC ............................................................ 310/334
See application file for complete search history.

(56) References Cited

U.S. PATENT DOCUMENTS 4,641,520 A * 2/1987 Mao ........................... 73/152.58
5,016,474 A    5/1991 Hazony et al.
5,140,860 A    8/1992 Hueschelrath et al.
(Continued)

FOREIGN PATENT DOCUMENTS

| DE | 4304548 | 10/1993 |
| EP | 0171118 | 2/1986 |
| EP | 1698894 | 9/2006 |
| EP | 2036620 | 3/2009 |
| GB | 2152668 | 8/1985 |

OTHER PUBLICATIONS

International Search Report and Written Opinion from International application No. PCT/GB2011/050395, issued Apr. 2, 2012.
(Continued)

*Primary Examiner* — J. San Martin
(74) *Attorney, Agent, or Firm* — Stroock & Stroock & Lavan LLP (57) ABSTRACT

An ultrasonic transducer includes a wear plate (2), a piezoelectric element (8) arranged rearwards of the wear plate and a rigid block (16) arranged rearwards of the piezoelectric element and configured to provide a backing mass for the piezoelectric element. The wear plate extends across the piezoelectric element and rearwards so as to provide a cap over the piezoelectric element and sides of at least a forward portion of the rigid block.

12 Claims, 7 Drawing Sheets

(56) References Cited

U.S. PATENT DOCUMENTS

| | | |
|---|---|---|
| 5,176,034 A | 1/1993 | Hazony et al. |
| 5,619,423 A | 4/1997 | Scrantz |
| 2007/0151344 A1 | 7/2007 | Meethal et al. |
| 2009/0158850 A1* | 6/2009 | Alleyne et al. ................. 73/623 |
| 2010/0275693 A1* | 11/2010 | Zhuang et al. ................. 73/632 |

OTHER PUBLICATIONS

Great Britain Search Report from Great Britain application No. GB 1006571.2, issued Jul. 2, 2010.

* cited by examiner

Fig. 11

TRANSDUCER ASSEMBLY

CROSS-REFERENCE TO RELATED APPLICATIONS

This application is a national stage application under 35 U.S.C. 371 based on and claiming the benefit of International Application Ser. No. PCT/GB2011/050395, filed on Feb. 28, 2011, which claims the benefit of priority from United Kingdom Patent Application No. 1006571.2, filed on Apr. 20, 2010 and United Kingdom Patent Application No. 1015609.9, filed on Sep. 17, 2010, the entire contents of each of which are incorporated herein by reference.

FIELD OF THE INVENTION

The present invention relates to an ultrasonic transducer particularly, but not exclusively, for use in inspecting pipes using guided ultrasonic waves.

BACKGROUND

Ultrasonic waves can be used for inspecting a structure, such as a pipe, to identify defects and flaws within the structure. Examples of ultrasonic inspection devices can be found in WO 96/12951 A, WO 2007/125308 A2 and EP 1 394 538 A1

WO 96/12951 A describes apparatus for inspecting elongate members, such as pipes. The apparatus includes a ring of angularly-spaced transducers (or "exciters") clamped to the outside wall of a pipe. Each transducer includes a piezoelectric element, a metal block adhesively bonded to the piezoelectric element, and a thin faceplate shim secured to the face of the piezoelectric element to provide a wear plate.

In the prior art transducer, the piezoelectric element and wear plate are stacked in a recess in the metal block and secured using an epoxy adhesive. This arrangement can have disadvantages.

Firstly, the sides of the wear plate may be constrained by the sides of the recess. This can decrease the efficiency of the transducer.

Secondly, the metal block is near the pipe. If the pipe is hot, then the metal block can absorb heat radiated by the pipe and heat the piezoelectric element and the epoxy adhesive. Piezoelectric elements have a maximum operating temperature and so this arrangement can limit the maximum temperature of pipe that can be inspected using the transducer.

Thirdly, when inspecting a hot pipe, both the front of the metal block and the wear plate are exposed to high temperatures. If the metal block and wear plate are made from different materials, then they may expand at different rates dues to different coefficients of thermal expansion. This can limit the maximum operating temperature of the transducer and reduce the number of operation cycles.

Finally, the bond line between the metal block and the wear plate is at the front of the transducer and so is usually exposed to the environment. This can limit the lifetime of the transducer and/or make it less reliable due to exposure to the environment, for example due to ingress of sea water. Furthermore, if the pipe is hot, then the epoxy adhesive is directly exposed to heating.

SUMMARY

The present invention seems to provide an improved ultrasonic transducer.

According to the present invention there is provided an ultrasonic transducer including a wear plate, a piezoelectric element arranged rearwards of the wear plate and a rigid block arranged rearwards of the piezoelectric element and which is configured to provide a backing mass for the piezoelectric element, wherein the wear plate extends across the piezoelectric element and rearwards so as to provide a cap over the piezoelectric element and sides of at least a forward portion of the rigid block.

This transducer can have one or more advantages. The arrangement can allow the wear plate to move more freely and, thus, increase the efficiency of the transducer. Furthermore, the wear plate can shield the metal block from a hot structure, such as a hot pipe. Thus, if the wear plate is made from a material which is a poor thermal conductor, this can allow a hotter structure to be inspected and/or to be inspected for longer. Moreover, the region of the transducer which is closest to the structure under inspection is made from the same material which can help to reduce the problem of different parts expanding at different rates. In addition, a larger piezoelectric element can be used since it is not constrained by the size of a recess in the backing mass.

The wear plate can have a forward face and rearwards face, wherein the forward face is shaped to provide a knife edge. This can allow the wear plate to cut through or pierce a coating covering a pipe and contact an underlying structure.

The wear plate can comprise a material which is material which is a poor thermal conductor, such as a ceramic. This can help to reduce heating of the piezoelectric element if the transducer is in contact with a hot object.

The wear plate may comprise a laminate including a layer of ceramic and/or metal or metal alloy.

The wear plate may have a thickness of at least 1 mm.

The ultrasonic transducer may further comprise a thermally-conductive element disposed between the wear plate and the piezoelectric element for conducting heat absorbed by the wear plate. The thermally-conductive element comprises a layer of thermally-conductive material disposed on a rearward surface of the wear plate. This can help to reduce heating of the piezoelectric element if the transducer is in contact with a hot object.

The piezoelectric element may be a shear polarised piezoelectric element.

The ultrasonic transducer may further comprise another piezoelectric element. The other piezoelectric element may be arranged between the piezoelectric element and the rigid block in a stack. Thus, different orientations or magnitudes of motion can be generated.

The ultrasonic transducer may further comprise a filler, such as an adhesive, arranged to encapsulate the piezoelectric element and the forward portion of the rigid block.

According to a second aspect of the present invention there is provided apparatus for inspecting an elongate member, the apparatus comprising a plurality of ultrasonic transducers, the ultrasonic transducers may be arranged in a band around the elongate member.

The apparatus may be configured to inspect a pipe and the ultrasonic transducers may be angularly spaced in a ring around an exterior wall of the pipe.

According to a third aspect of the present invention there is provided a method of operating the ultrasonic transducer comprising placing the wear plate in contact with the elongate member and applying an electrical signal to the piezoelectric element. The ultrasonic transducer may be urged against the elongate member.

BRIEF DESCRIPTION OF THE DRAWINGS

Certain embodiments of the present invention will now be described, by way of example, with reference to the accompanying drawings in which.

DETAILED DESCRIPTION OF CERTAIN EMBODIMENTS

In the following, like parts are denoted by like reference numerals.

Referring to FIGS. 1, 2, 2a, 3 and 4, an ultrasonic transducer assembly 1 (herein simply referred to as an "ultrasonic transducer") is shown.

Figure 1:
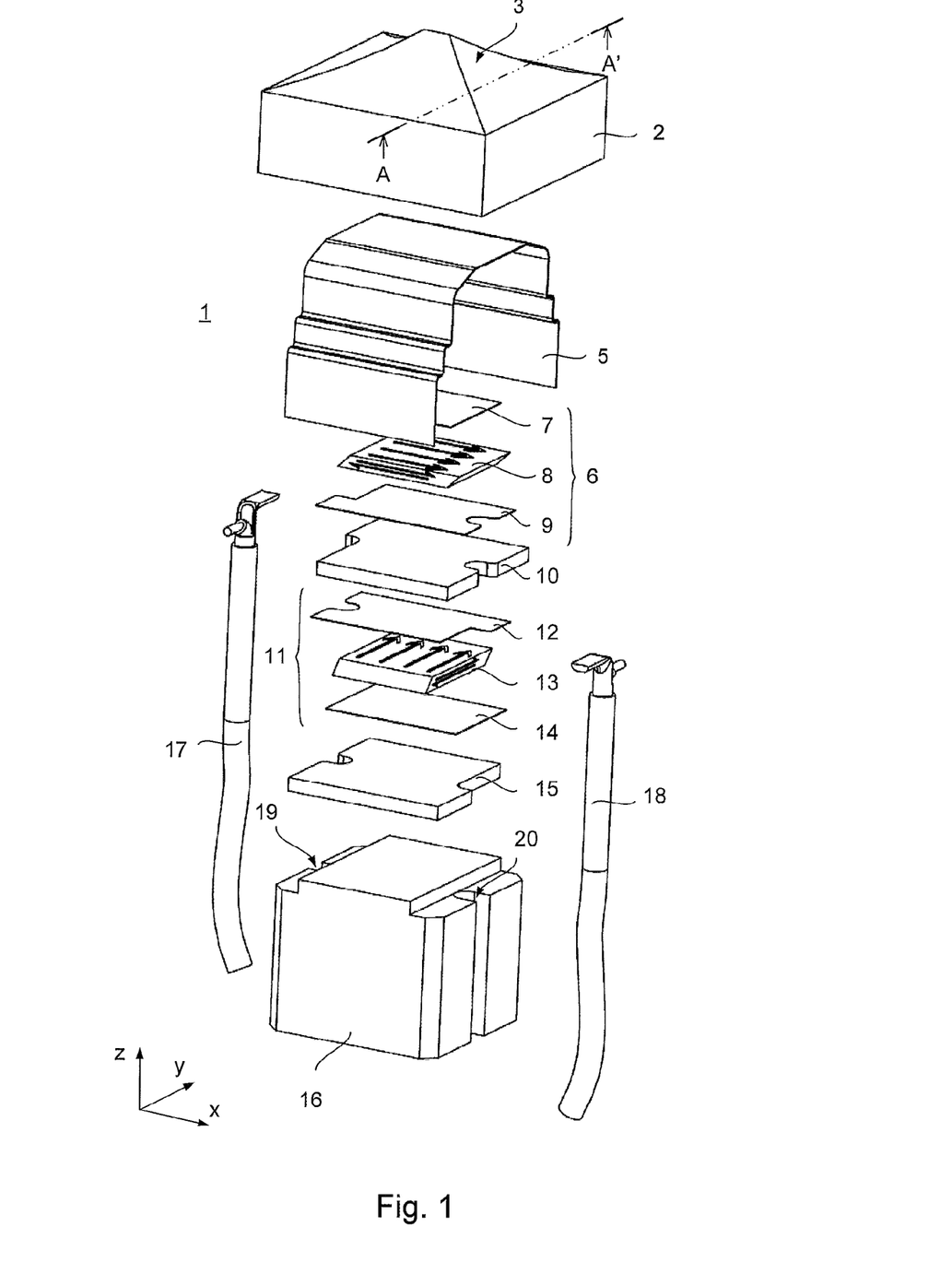
FIG. 1 is an exploded perspective view of an ultrasonic transducer assembly.
Figure 2:
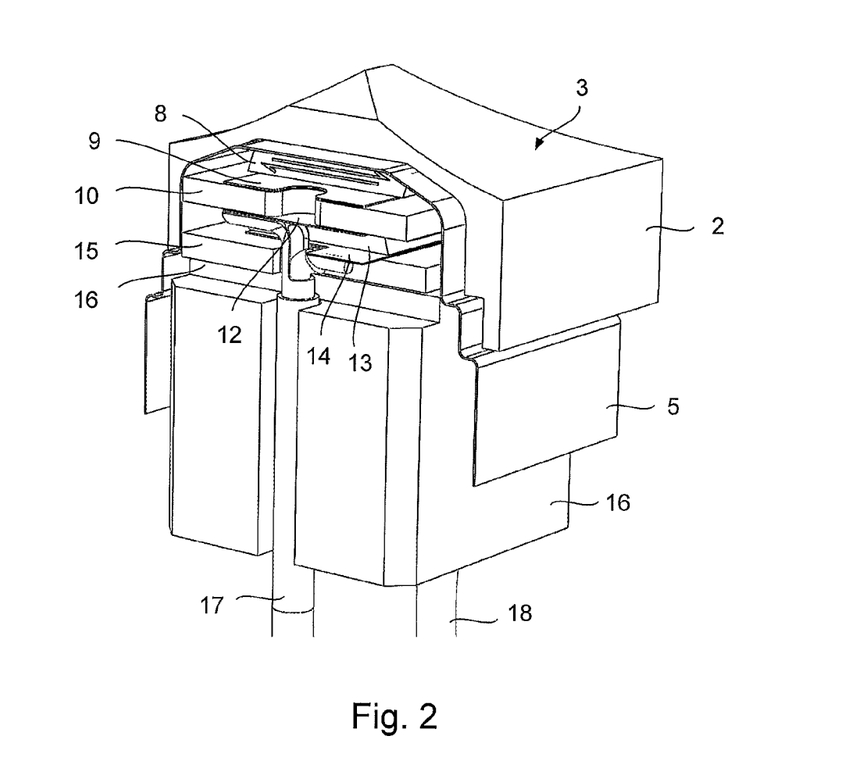
FIG. 2 is a part cutaway perspective view of the ultrasonic transducer shown in FIG. 1.
Figure 2A:
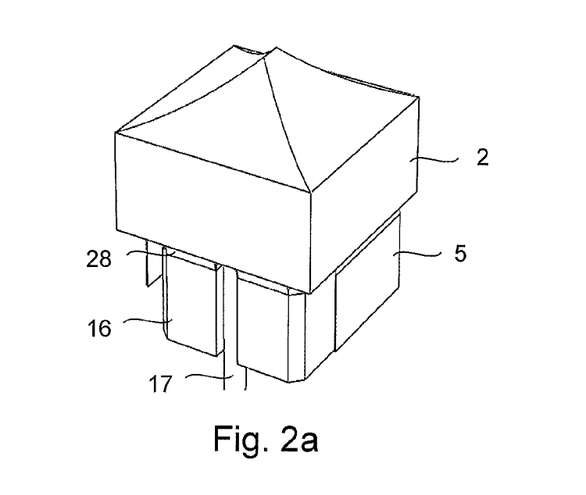
FIG. 2a is a perspective view of the ultrasonic transducer shown in FIG. 1.
Figure 6:
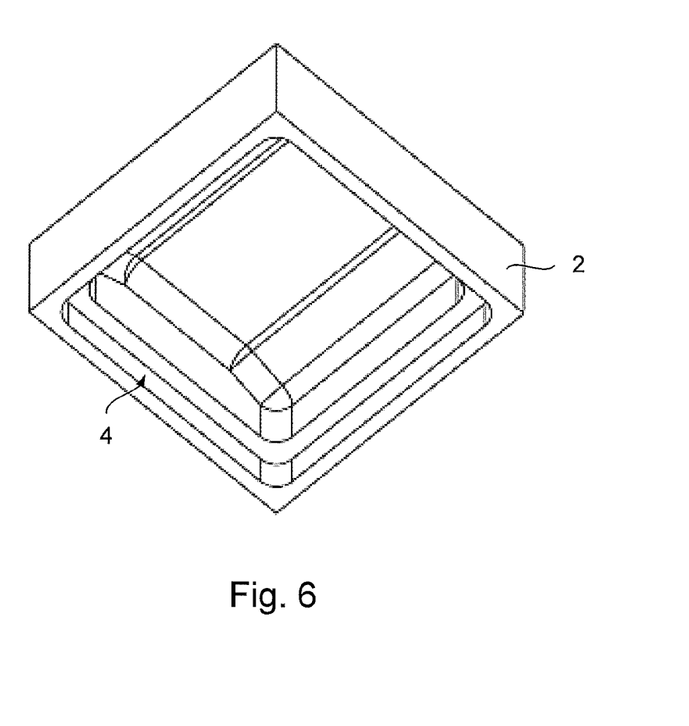
FIG. 6 is a perspective view of the wear plate shown in FIG. 5 from below.

The ultrasonic transducer 1 includes a wear plate 2 (which may also be referred to as a "face plate" or "contact head") having a front surface 3 which, in use, is pressed into contact with an object or structure (not shown) under inspection, and a rear surface 4 (FIG. 6). The wear plate 2 is made from a ceramic, such as zirconium dioxide ($ZrO_2$) or aluminium oxide ($Al_2O_3$), or other suitable material which is a poor thermal conductor. The material may have a value of thermal conductivity, k, equal to or less than 25 $Wm^{-1}K^{-1}$, equal to or less than 10 $Wm^{-1}K^{-1}$, equal to or less than 5 $Wm^{-1}K^{-1}$ or equal to or less than 2 $Wm^{-1}K^{-1}$. However, in some embodiments, the wear plate 2 can be made from a metal or a metal alloy. An arched heat-extracting strip 5 (or "heat sink") runs behind the wear plate 2. The strip 5 comprises a metal or thermally highly-conductive material, such as copper, aluminium, gold or silver. The material may have a value of thermal conductivity, k, equal to or greater than 200 $Wm^{-1}K^{-1}$. The heat-extracting strip 5 can be omitted, particularly if the object or structure under inspection is at or close to ambient temperature.

The ultrasonic transducer 1 includes a first transducer stack 6 which comprises a first earth electrode 7 which is closest to the wear plate 2, a first active layer 8 in the form of a shear polarized piezoelectric layer and a first signal electrode 9.

A first electrical insulating layer or plate 10 separates the first transducer stack 6 from a second transducer stack 11. The second transducer stack 11 comprises a second earth electrode 12, a second active 13 layer also in the form a shear polarized piezoelectric layer and a second signal electrode 14.

A second electrical insulating layer 15 separates the second transducer stack 11 from a rigid block 16 which provides a non-resonant backing mass. The rigid block 16 is preferably made of steel or other dense material so as to provide a high mass. The material may be chosen so as to have a low coefficient of thermal expansion or one which is matched to the wear plate.

First and second miniature coaxial cables 17, 18 provide connections to the first and second pairs of electrodes 7, 9, 12, 14 respectively. The cables 17, 18 sit in recesses 19, 20 running down opposite sides of the rigid block 16.

As shown in FIG. 1, the piezoelectric elements 8, 13 are stacked such that their polarizations cross, e.g. perpendicularly, by rotating the direction of one layer 8 relative to the other 13 and are separately controlled. Being able to generate different orientations of shear motion, e.g. along the x-axis or along the y-axis, allows different types of guided wave modes to be generated and received by the transducer 1, thereby avoiding the need for two different sets of transducer elements for the different orientations.

Notwithstanding this, the piezoelectric elements 8, 13 can be stacked having the same polarization and wired in parallel in order to increase the maximum deflection generated by a given voltage. This can increase the signal-to-noise ratio by injecting larger signals into the pipe.

Moreover, as will be shown later, the transducer need only have one piezoelectric element. Thus, for example, the second transducer stack 11, second electrical insulating layer 15 and second coaxial cable 18 can be omitted.

Figure 3:
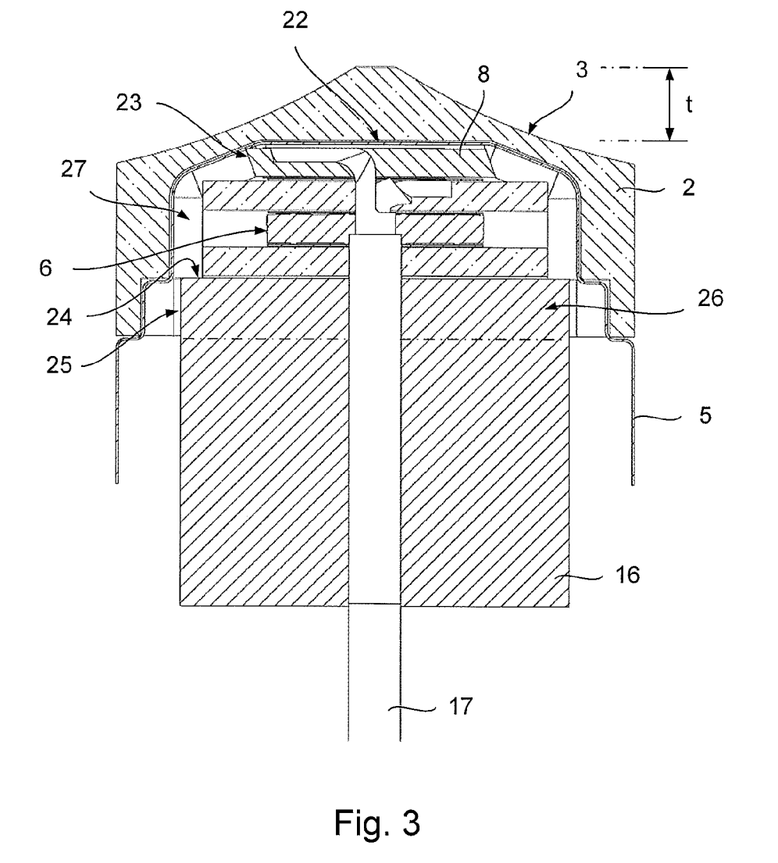
FIG. 3 is a cross sectional view of the ultrasonic transducer shown in FIG. 1 taken along the line A-A'.

Referring in particular to FIG. 3, the wear plate 2 passes in front (as shown, the top) of the rest of the transducer and to the rear (as shown, down) to provide a cap over a forward-most portion of the heat-extracting strip 5, the transducer stacks 6, 11 and the insulating plates 10, 15. The wear plate 2 also extends beyond a front face 24 of the rigid block 16 and along the sides 24 of a forward portion (as shown, a top portion) of the rigid block 16.

The wear plate 2 is shaped to provide a space or recess 27 in which the forward-most portion of the heat-extracting strip 5, the transducer stacks 6, 11, the insulating plates 10, 15 and the top part of the rigid block 16 sit. The wear plate 2 may be machined or moulded.

The wear plate 2 may have a thickness, t, of material equal to or greater than 1 mm or equal to or greater than 2 mm. As shown in FIG. 3, the thickness, t, is behind the point (or region) which comes into contact with the structure under test. In this example, the thickness is in the middle of the wear plate 2 and is where the wear plate 2 is thickest. The wear plate 2 may be thinner where it is not in contact with the structure under test. Increasing the thickness of the wear plate 2 between the point of contact and the active layer 8 can help to increase thermal insulation and, thus, reduce heating of the active layer 8.

Figure 4:
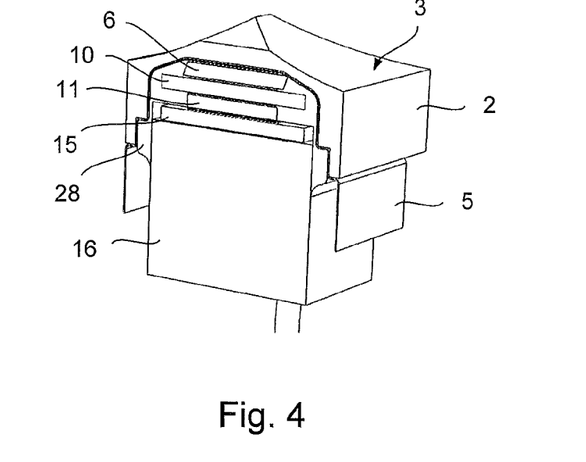
FIG. 4 is a part cutaway perspective view of an encapsulated ultrasonic transducer.

Referring in particular to FIG. 4, the rest of the space 27 (FIG. 3) is filled with a flexible filler 28 (hereing also referred to as an "encapsulate"), for example an epoxy adhesive or potting compound, so as to encapsulate the forward-most portion of the heat-extracting strip 5, transducer stacks 6, 11, insulating plates 10, 15 and the top part of the rigid block 16. The filler 28 may be a poor thermal conductor.

Referring still to FIGS. 1, 2, 2a, 3 and 4, the transducer 1 can be used in an apparatus or method for inspecting pipes as described in WO 96/12951 A and WO 2007/125308 A2 which are incorporated herein by reference.

The transducer 1 can offer several advantages, particularly when inspecting hot pipe and/or being used in harsh environments.

When the front 3 of the wear plate 2 is presented to a hot object, such as a hot pipe, the wear plate 2 can shield the rigid block 16 from heat. Furthermore, the part of the transducer 1 that is closest to the hot pipe—and which suffers the largest rapid temperature rise—is made from the same material. Thus, it is possible to sustain a large temperature gradient across the thickness (along the z-direction) of the wear plate 2.

The heat-extracting strip 5 allows heat to be transmitted away from the piezoelectric layers 8, 13. One or both ends of the strip 5 can be connected to a heat sink or heat exchange (not shown). This arrangement can help to protect sensitive piezoelectric layers 8, 13 from high temperatures.

The underside of the wear plate 2, the forward-most portion of the heat-extracting strip 5, transducer stacks 6, 11, insulating plates 10, 15 and forward-most portion of the rigid block 16 can be encapsulated to provide a watertight seal. In fact, the entire transducer, with the exception of a small portion of the wear plate 2 around a contact region, can be completely encapsulated to further enhance environmental protection.

Because the active element is not fitted inside a recess in the rigid block, a larger active element can be used. For example, the area of the active element can be as large as the rigid block. This can aid assembly, as well as improving efficiency of the transducer.

The front 3 of the wear plate 2 can be shaped to have a specific profile. For example, this can provide greater freedom of movement for the wear plate 2. Furthermore, the shape of the front 3 of the wear plate 2 can be optimised to maximise the use of air flow (or flow of some other fluid) to cool the transducer 1. For example, the shape of the front 3 of the wear plate 2 can be arranged so as maximise its surface area. Thus, air can be blown across the front 3 of the wear plate 2 to cool it. Moreover, the profile of the front 3 of the wear plate 2 can be configured, e.g. by keeping it smooth, to reduce turbulent air flow which can generate noise.

The shape of the front 3 of the wear plate 2 can be changed in order to modify the contact area with a pipe.

Figure 5:
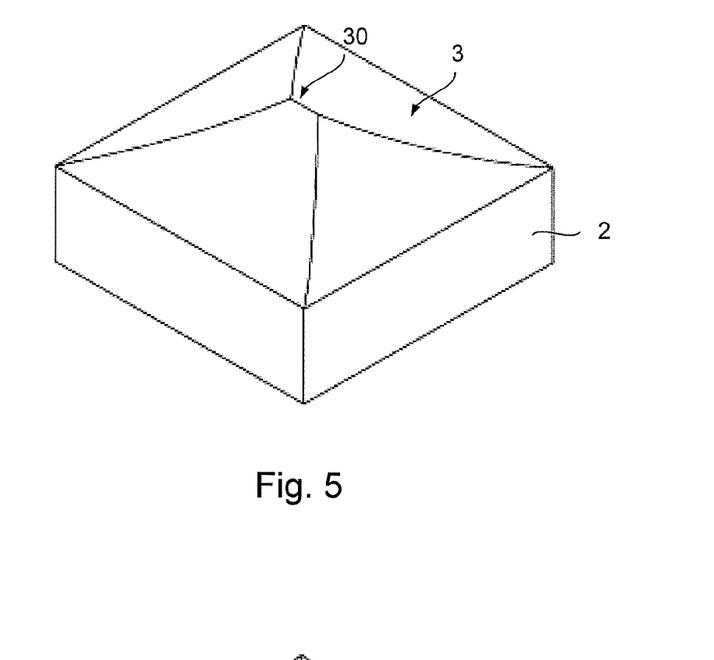
FIG. 5 is a perspective view of a wear plate having a knife edge contact region from above.

Referring in particular to FIG. 5, the wear plate 2 can be shaped to provide a sharp contact area 30, for example, in the form of a knife edge or sharp ridge. This allows the wear plate 2 to cut through or pierce a plastic coating (not shown) covering a pipe (not shown) and contact an underlying metal wall of the pipe (not shown). Preferably, the wear plate 2 comprises a tough material, such as a hard, non-brittle ceramic, a metal or metal alloy, such as stainless steel or tungsten carbide. As mentioned earlier, the wear plate 2 may comprise a ceramic, such as $ZiO_2$ or $Al_2O_3$, or other suitable material which is a poor thermal conductor. The wear plate 2 can be a laminate, e.g. comprising a metal layer and an overlying layer of ceramic. The wear plate 2 may have a thickness, t, equal to or greater than 1 mm or equal to or greater than 2 mm.

In FIG. 6, the wear plate 2 is shown from the rear. The rear surface 4 of the wear plate 2 provides a recess having a stepped wall.

The axial contact length can be smaller than the diameter of the rigid block 16 (FIG. 1). A narrow contact profile allows the transducer to be tilted more.

Figure 7:
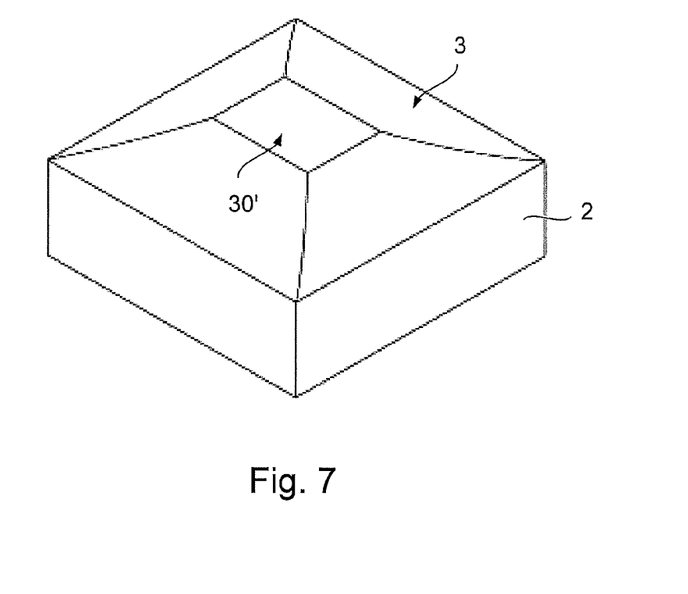
FIG. 7 is a perspective view of a wear plate having a blunt contact region from above.
Figure 8:
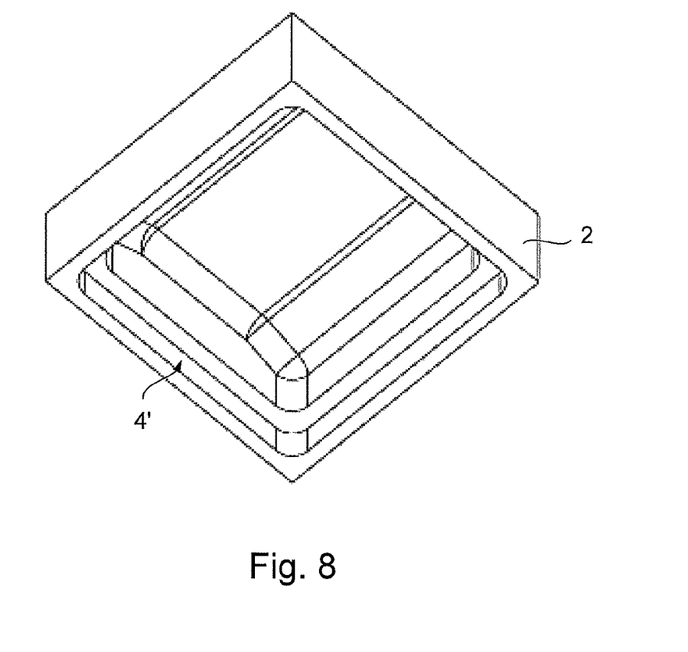
FIG. 8 is a perspective view of the wear plate shown in FIG. 7 from below.

Referring in particular to FIG. 7, a modified wear plate 2' is shown which is shaped to provide a wide contact area 30'. This can be used to increase coupling between the pipe and the transducer.

As explained earlier, the transducer need not include a heat-extracting strip 5 (FIG. 1) or a second piezoelectric layer 13 (FIG. 1). For example, the heat-extracting layer can be omitted if the transducer is to be used to inspect cool objects.

Figure 9:
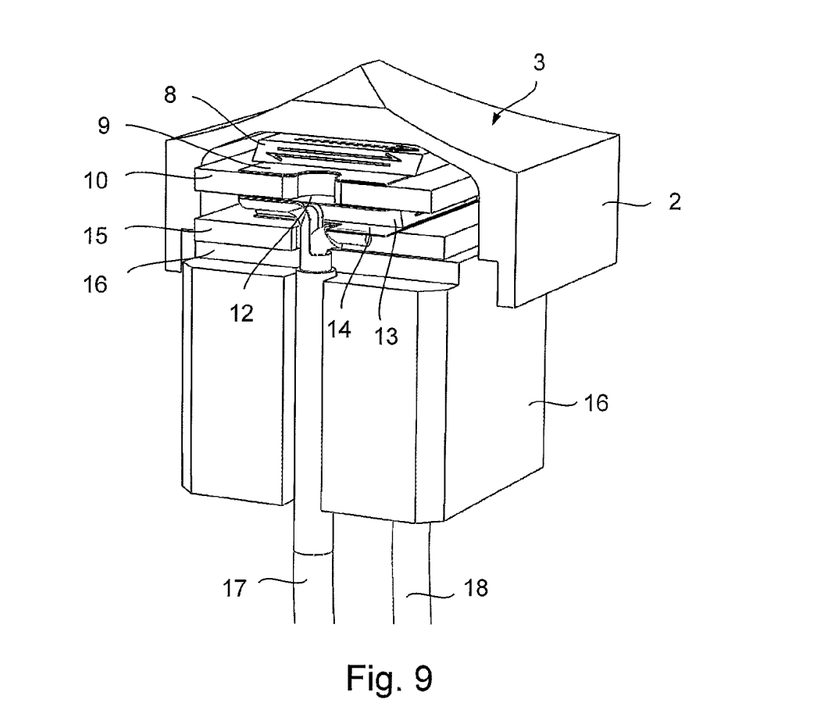
FIG. 9 is a part cutaway perspective view of an ultrasonic transducer without a heat-extracting strip.

FIG. 9 shows another transducer 1'. The transducer 1' is similar to the transducer 1 (FIG. 1) described earlier, but does not have a heat-extracting layer.

Figure 10:
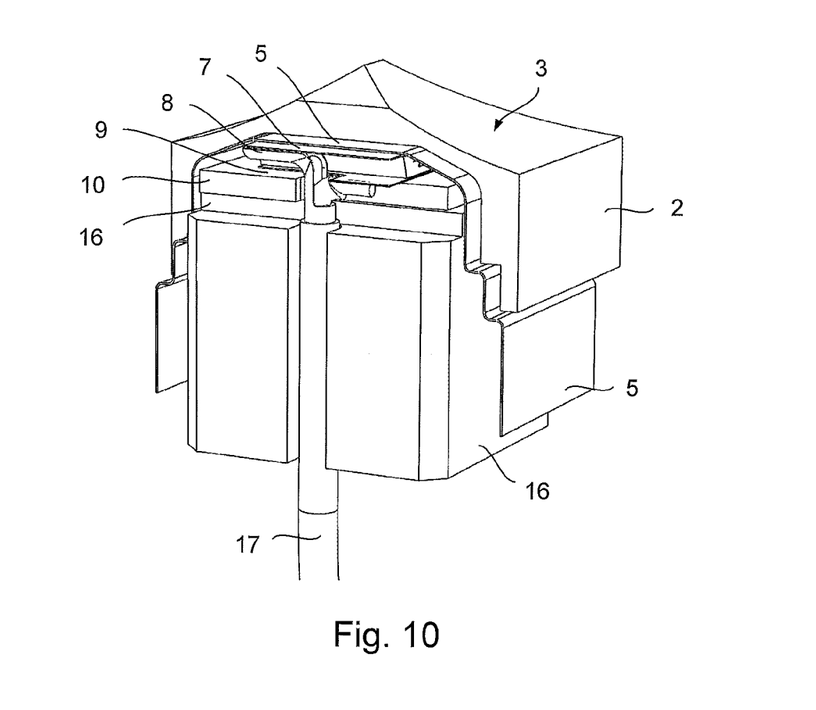
FIG. 10 is a part cutaway perspective view of an ultrasonic transducer with a single active element and a heat-extracting strip.

FIG. 10 shows yet another transducer 1''. The transducer 1'' is similar to the transducer 1 (FIG. 1) described earlier, but has only one piezoelectric layer 10. Thus, the transducer 1'' does not have a second transducer stack 11 including the second earth electrode 12, the second active 13 layer and the second signal electrode 14. The transducer 1'' also does not have a second electrical insulating layer 15 and a second coaxial cable 18.

Figure 11:
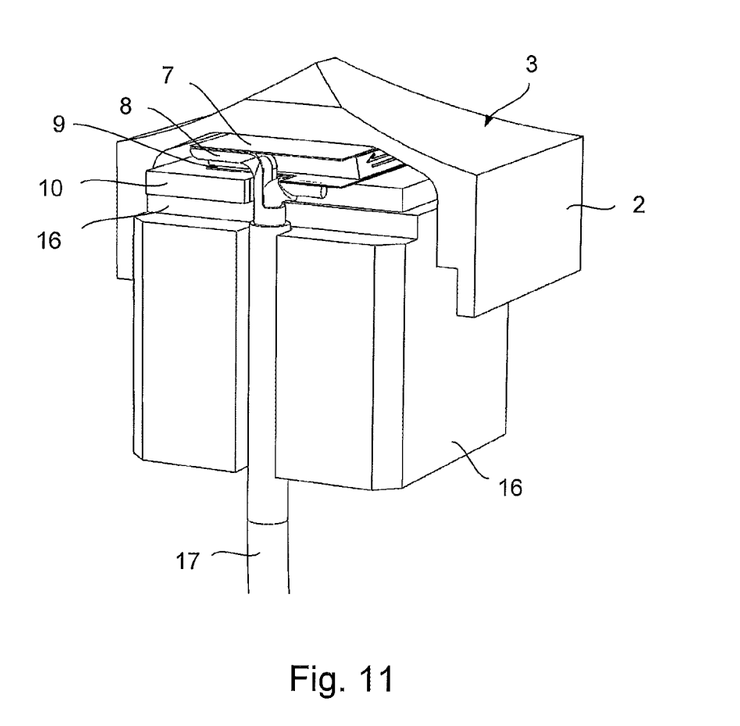
FIG. 11 is a part cutaway perspective view of an ultrasonic transducer with a single active element and without a heat-extracting strip.

FIG. 11 shows still yet another transducer 1'''. The transducer 1'' is similar to the transducer 1'' (FIG. 10) described earlier, but does not have a heat-extracting layer.

It will be appreciated that many modifications may be made to the embodiments hereinbefore described.

For example, in some of the embodiments, a heat-extracting strip is used. Additionally or alternatively, the rear 4 (FIG. 3) of the faceplate 2 can be coated, e.g. by electroplating, with a highly thermally-conductive coating, such as copper.

The ultrasonic transducer may be a different type of direct contact ultrasonic transducer.

The wear plate may be made as thick as possible provided it still transmits significant force across the interface into the test component.

The invention claimed is:

1. An ultrasonic transducer including:
   a wear plate;
   a piezoelectric element arranged rearwards of the wear plate; and
   a rigid block arranged rearwards of the piezoelectric element and configured to provide a backing mass for the piezoelectric element;
   wherein the wear plate extends across the piezoelectric element and rearwards so as to provide a cap over the piezoelectric element and sides of at least a forward portion of the rigid block; wherein the wear plate has a forward face and rearwards face and, wherein the piezoelectric element is a shear-polarized piezoelectric element and the forward face is shaped to provide a knife edge or sharp ridge.

2. An ultrasonic transducer according to claim 1, wherein the wear plate comprises a material which is a poor thermal conductor.

3. An ultrasonic transducer according to claim 1, wherein the wear plate comprises a ceramic.

4. An ultrasonic transducer according to claim 1, further comprising a thermally-conductive element disposed between the wear plate and the piezoelectric element for conducting away heat absorbed by the wear plate.

5. An ultrasonic transducer according to claim 3, wherein thermally-conductive element comprises a layer of thermally-conductive material disposed on rearwards surface of the wear plate.

6. An ultrasonic transducer according to claim 1, wherein the wear plate has thickness of at least 1 mm.

7. An ultrasonic transducer according to claim 1, further comprising another piezoelectric element.

8. An ultrasonic transducer according to claim 6, wherein the other piezoelectric element is arranged between the piezoelectric element and the rigid block in a stack.

9. An ultrasonic transducer according to claim 1, further comprising a filler, such as an adhesive, arranged to encapsulate the piezoelectric element and the forward portion of the rigid block.

10. Apparatus for inspecting an elongate member, the apparatus comprising a plurality of ultrasonic transducers according to claim 1, the ultrasonic transducers arranged in a band around the elongate member.

11. Apparatus according to claim 8, wherein the apparatus is configured to inspect a pipe and the ultrasonic transducer are angularly spaced in a ring around an exterior wall of the pipe.

12. A method of operating a transducer according to claim 1 comprising:
 placing the wear plate in contact with the elongate member; and
 applying an electrical signal to the piezoelectric element.

* * * * *